United States Patent [19]

Wieland

[11] Patent Number: 4,622,217

[45] Date of Patent: Nov. 11, 1986

[54] I-4-AMINO-3-IODOBENZYLGUANIDINE AS IMAGING AND THERAPEUTIC AGENT

[75] Inventor: Donald M. Wieland, Ann Arbor, Mich.

[73] Assignee: The Regents of the University of Michigan, Ann Arbor, Mich.

[21] Appl. No.: 604,383

[22] Filed: Apr. 27, 1984

[51] Int. Cl.$^4$ .................. G01N 43/00; G01N 49/00
[52] U.S. Cl. ........................... 424/1.1; 424/9; 564/237
[58] Field of Search ............ 424/1.1, 9; 564/237

[56] References Cited

U.S. PATENT DOCUMENTS

| 4,022,877 | 5/1977 | Huber et al. | 424/1.1 |
|---|---|---|---|
| 4,083,947 | 4/1978 | Monks et al. | 424/1.1 |
| 4,215,045 | 7/1980 | Knapp, Jr. | 424/1.1 |

OTHER PUBLICATIONS

"Adrenal Imaging Agents: Rationale, Synthesis, Formulation and, Metabolism", by W. H. Beierwaltes, et al, Seminars in Nuclear Medicin, vol. VIII, No. 1, Jan. 1978, p. 5.
"Imaging the Primate Adrenal Medullae with [$^{123}$I] and [$^{131}$I]Meta-Iodobenzylguanidine" by, Donald M. Wieland, Ph.D., Lawrence E. Brown, B.S., W. Leslie Rogers, Ph.D., David D. Marsh, Thomas J. Mangner, Ph.D., Dennis P. Swanson, M.S., W. H. Beierwaltes, M.D.
"Evolution of Pheochromocytoma in Multiple Endocrine Neoplasia: A Scintigraphic Portrayal Using $^{131}$I--Metaiodobenzylguanidine" by Timothy W. Valk, M.D., Marc S. Frager, M.D., Milton D. Gross, M.D., James C. Sisson, M.D., Donald M. Wieland, Ph.D., Dennis Swanson, M.S., William H. Beierwaltes, M.D.
"Scintigraphic Localization of Pheochromocytoma" by James C. Sisson, M.D., Marc S. Frager, M.D., Timothy W. Valk, M.D., Milton D. Gross, M.D., Dennis P. Swanson, M.S., Donald M. Wieland, Ph.D., Michael C. Tobes, Ph.D., William H. Beierwaltes, M.D., Norman W. Thompson, M.D.
"Myocardial Imaging in Man with $^{123}$I-Meta-Iodobenzylguanidine", by Robert C. Kline, M.D. Dennis P. Swanson, M.S., Donald M. Wieland, Ph.D., James H. Thrall, M.D., Milton D. Gross, M.D., Bertram Pitt, M.D., and William H. Beierwaltes, M.D.
Abstract entitled $^{123}$-I-m-Iodobenzylguanidine, A New Agent for Imaging the Human Myocardium",by R. C. Kline, D. P. Swanson, D. M. Wieland, J. H. Thrall, M. D. Gross, B. Pitt, W. H. Beierwaltes, "Circulation", vol. 62, Supp III, Oct. 1980.
Imaging the Primate Adrenal Medulla with [$^{123}$I] and [$^{131}$I] Meta-Iodobenzylguanidine: Concise Communication, by D. M. Wieland, L. E. Brown, M. C. Tobes, W. L. Rogers, D. D. Marsh, T. J. Mangner, D. P. Swanson, and W. H. Beierwaltes, "The Journal of Nuclear Medicine, vol. 22, No. 4, p. 358.
1981 Abstract Form for Scientific Papers and Scientific Exhibits of Society of Nuclear Medicine 28th Annual Meeting, entitled "A New Radioiodide Exchange Technique: The MW2 Method., by T. J. Mangner, J. L. Wu, D. M. Wieland and W. H. Beierwaltes.
Myocardial Imaging in Man with I-123 Meta-Iodobenzylguanidine by R. C. Kline, D. P. Swanson, D. M. Wieland, J. H. Thrall, M. D. Gross, B. Pitt, and W. H. Beierwaltes, "Journal of Nuclear Medicine," vol. 22, 1981, pp. 129-132.
Imaging the Adrenal Medulla with an I-131-Labeled Antiadrenergic Agent, by D. M. Wieland, D. P. Swanson, L. E. Brown, W. H. Beierwaltes, reprinted from the Journal of Nuclear Medicine, Feb., 1979, vol. 20, No. 2, pp. 155-158.
1981 Abstract Form for Scientific Papers and Scientific Exhibits for the Society of Nuclear Medicine 28th Annual Meeting, entitled "Localization of Pheochromocytomas with I-131-M-Iodobenzylguanidine (I-131-MIBG), by M. Gross, M. Frager, T. Valk, R. Kline, J. Sisson, D. Swanson, D. Wieland, N. Thompson, M. Tobes, W. Beierwaltes.
1981 Abstract Form for Scientific Papers & Scientific Exhibits for Society of Nuclear Medicine 28th Annual Meeting, entitled, "The Mechanism of m-IBG Localization: Drug Intervention Studies, by D. M. Wieland, L. E. Borwn, D. D. Marsh, T. J. Mangner W. H. Beierwaltes with 4 pages of supporting data.
Wieland et al, T. Med. Chem. 27(1984) 149–155.

Primary Examiner—Christine M. Nucker
Attorney, Agent, or Firm—Harness, Dickey & Pierce

[57] ABSTRACT

A novel compound, 4-amino-3-iodobenzylguanidine, in radioiodinated form is useful in radiopharmaceutical compositions in nuclear medicine as an imaging agent for the heart, adrenal medulla, and tumors of the adrenal medulla and can be used for treatment of tumors of the adrenal medulla. The radioactive compound can be readily made by reacting 4-aminobenzylguanidine and an N-chloro oxidant in the presence of a radioiodide.

22 Claims, No Drawings

I-4-AMINO-3-IODOBENZYLGUANIDINE AS IMAGING AND THERAPEUTIC AGENT

BACKGROUND OF THE INVENTION

The present invention relates to radiolabeled compounds, their method of making, and their method of use in clinical nuclear medicine. More specifically, the present invention relates to a novel compound, iodinated 4-amino-3-iodobenzylguanidine which in radioiodinated form can be used in a radiopharmaceutical composition as an imaging agent, particularly for the heart, adrenal medulla, and tumors of the adrenal medulla as well as a treatment agent for tumors of the adrenal medulla. The present invention also relates to a method of synthesis and a kit for synthesis of the radioiodinated compound of this invention.

Radiolabeled compounds which are subject to localization in particular organs or tumors therein are of great value for diagnosis and/or therapeutic purposes for diseases of the human body. For example, Thallium-201 and fatty acids labeled with carbon-11 and iodine-123 have been utilized as heart imaging agents. Also, various phosphonate ligands labeled with technetium-99m have been used to image infarcted regions of the heart. However, although many useful radiolabeled compounds are known, there remains a need for the discovery of improved compounds which are effective for routine imaging of particular organs, tissues, or tumors therein. In addition, there remains a need for radiolabeled compounds which are useful in treating tumors of specific organs of the human body.

The agent meta-iodobenzylguanidine labeled with iodine-131 or iodine-123 has been found to image the adrenal medulla and tumors of the adrenal medulla and is disclosed in copending U.S. patent application of Wieland, et al., Ser. No. 250,059 filed Apr. 1, 1981 for "Imaging Agent and Method of Use", as well as in articles cited therein and in Lynn, et al., "Portrayal of Pheochromocytoma and Normal Human Adrenal Medulla by M-[$^{123}$I] Iodobenzylguanidine: Concise Communication", *J. Nucl. Med.* 25:436–440, 1984. There remains a need, however, for an agent which can be more easily synthesized in radioiodinated form than radioiodinated meta-iodobenzylguanidine.

There also remains a need for an improved imaging agent for the heart. The above-mentioned radioiodinated meta-iodobenzylguanidine gives images of the heart but the synthetic difficulty and general unavailability of this agent have limited its clinical use. Furthermore, it would be desirable to have an imaging agent having a higher degree of selectivity for the adrenergic nerves of the heart than radioiodinated meta-iodobenzylguanidine. Thallium-201 is used for heart imaging, but it is expensive and has less than optimum nuclear imaging properties. Carbon-11 fatty acids can be used for heart imaging but their use is severely limited by the requirement for an in-house cyclotron for the product of the short-lived isotope (T1/2=20 min) C-11. The use of iodine-123 fatty acids is still being evaluated in various nuclear medicine clinics throughout the world, but these compounds have a short biologic T1/2 (about 10 minutes) in the heart. Technetium-99m labeled disphosphonates are useful heart imaging agents but are not heart perfusion agents and are limited to imaging only severely damaged or infarcted regions of the heart.

In accordance with the present invention, a novel iodinated compound is provided. The novel iodinated compound can be synthesized in radioiodinated form, and can be readily synthesized by means of the kit and method of synthesis of this invention. A radiopharmaceutical composition comprising the radioiodinated compound can be used as an exceptional imaging agent, particularly for the adrenal medulla, tumors of the adrenal medulla and the heart. The radioiodinated compound has a high degree of selectivity for the adrenergic nerves of the heart. A radiopharmaceutical composition comprising the radioiodinated compound can also be used for the diagnosis and/or treatment of tumors, particularly tumors of the adrenal medulla.

SUMMARY OF THE INVENTION

The present invention relates to a novel radiopharmaceutical compound, radioiodinated 4-amino-3-iodobenzylguanidine. In addition, the present invention relates to a kit and method for making the novel radioiodinated compound as well as to radiopharmaceutical compositions comprising the compound and their method of use as diagnostic or therapeutic compositions. A radiopharmaceutical composition of the present invention comprises radioiodinated 4-amino-3-iodobenzylguanidine and a pharmaceutical carrier such as a physiological buffered saline solution. A method for diagnostic imaging comprises the steps of systemically applying to a human an effective amount of a radiopharmaceutical composition comprising radioiodinated 4-amino-3-iodobenzylguanidine and subsequently making an image by detecting gamma radiation emitted by said radiological composition following its localization in the target organ. A method for treating tumors of the adrenal medulla comprises the step of systemically applying to a human an effective amount of a radiopharmaceutical composition comprising radioiodinated 4-amino-3-iodobenzylguanidine.

DESCRIPTION OF THE INVENTION

Despite the physiological importance of norepinephrine as an adrenergic transmitter, only the aforementioned radiopharmaceutical, meta-iodobenzylguanidine, heretofore has been used for assessing catecholamine hormone accumulation and turnover in peripheral tissue. It has now been discovered that 4-amino-3-iodobenzylguanidine which is an iodinated analog of guanethidine, is accumulated in adrenergic tissues in a manner similar to norepinephrine and guanethidine, an adrenergic neuronal blocking agent, and therefore localizes in the adrenergic neurons of the heart and chromaffin granules of the adrenal medulla. Accordingly, it has been discovered that radioiodinated 4-amino-3-iodobenzylguanidine is a useful radiopharmaceutical for imaging the heart, adrenal medulla, and tumors of the adrenal medulla.

Radioiodinated 4-amino-3-iodobenzylguanidine compounds suitable for use herein can be synthesized by an electrophillic radioiodination technique using an N-chloro oxidant and a radioiodine as illustrated in Examples I–III. The I-123 radiolabel is preferably employed as an imaging agent for the heart, adrenal medulla in human patients, and tumors of the adrenal medulla while the I-131 radiolabel, which has a longer half-life, is preferably employed as a therapeutic agent in human patients.

It is contemplated that the present invention will be provided to a nuclear pharmacist or a clinician in kit form. In accordance with the method of synthesis of this invention, the radioiodinated I-4-amino-3-iodobenzylguanidine can be readily made by a clinician or pharamacist at the location of intended use thus avoiding shipment of a premade radioiodinated compound. In accordance with the method of synthesis, radioiodinated 4-amino-3-iodobenzylguanidine can be made by reacting an N-chloro oxidant with 4-aminobenzylguanidine in the presence of a radioiodide. For example, 4-aminobenzylguanidine can be dissolved in a phosphate buffer, combined with the N-cloro oxidant whereupon radioiodide is added to the solution which is agitated and the reaction allowed to proceed. A suitable kit of the present invention comprises separate containers of an N-chloro oxidant and 4-aminobenzylguanidine. It is contemplated that the clinician or pharmacist will obtain radioiodide from a separate source. Suitable N-chloro oxidants include N-chloro-p-toluenesulfonamide, sodium salt and 1,3,4,6-tetrachloro-3γ,6γ-diphenylglycouril.

A pharmaceutical composition of the present invention comprises one of the aforementioned isotopes of radioiodinated 4-amino-3-iodobenzylguanidine and a carrier such as a physiological buffered saline solution a physiologically buffered sodium acetate carrier. It is contemplated that the composition will be systemically administered to the patient as by intravenous injection. Suitable dosages for use as a diagnostic imaging agent are from about 0.2 to about 2.0 mCi of I-131 labeled 4-amino-3-iodobenzylguanidine for the adrenal medulla or tumors therein, and from about 2.0 to about 10.0 mCiof the I-123 labeled agent for imaging of the heart and adrenal medulla or tumors therein. For use as a therapeutic agent, a higher dosage is required, for example, from about 100 to about 300 mCi of the I-131 labeled material.

It will be appreciated by those skilled in the art that the novel imaging agent of the present invention is employed in accordance with conventional methodology in nuclear medicine in a manner analogous to that of the aforementioned meta-iodobenzylguanidine. Thus, a composition of the present invention is systemically applied to the patient and subsequently the uptake of the composition in the selected organ is measured and an image formed, for example, by means of a conventional gamma camera.

Further understanding of use of the present invention can be obtained from the following examples and from Kline, et al.: "Myocardial Imaging in Man with [$^{123}$I]-Meta-Iodobenzylguanidine," *J. Nucl. Med.* 22:129–132, 1981; Wieland, et al: "Myocardial Imaging with a Radioiodinated Norepinephrine Storage Analog," *J. Nucl. Med.* 22:22–31, 1981; Valk, et al: "Spectrum of Pheochromocytoma in Multiple Endocrine Neoplasia: A Scintigraphic Portrayal Using $^{131}$I-Meta-Iodobenzylguanidine," *Ann. Intern. Med.*, Vol. 94, pp. 762–767 (1981); Sisson, et al.: "Scintigraphic Localization of Pheochromocytoma," *New Eng. J. Med.*, Vol. 305, pp. 12–17, (1981); and Lynn, et al., "Portrayal of Pheochromocytoma and Normal Human Adrenal Medulla by m-[I-123]-iodobenzylguanidine", *J. Nucl. Med.*, Vol. 25, Vol. 436–440 (1984); all of these articles are specifically incorporated by reference herein.

EXAMPLE I

I$^{131}$4-amino-3-iodobenzylguanidine was synthesized in accordance with the following procedure.

Part A

4-Nitrobenzylguanidine Sulfate

A mixture of 4-nitrobenzylamine [obtained by $CH_2Cl_2$ extraction of a mixture of 10 mmol of 4-nitrobenzylamine hydrochloride (from Aldrich Chemical Co. of Milwaukee, Wisc.) and 20 ml of 10% NaOH solution] and 2-methyl-2-thiopseudourea sulfate (1.40 g, 5.0 mmol) in water-ethanol (6 ml, 1:1 v/v) was heated and stirred in an oil bath at 110°–120° C. under argon for 40 hr. The solvents were evaporated and the residue was treated with boiling water (70 ml) and charcoal, filtered and concentrated to approximately 40 ml. On cooling, yellow crystals formed. They were filtered and washed with water. Recrystallization from water afforded an analytically pure sample (0.99 g, 41%), m.p. 244°–245° C. (dec.). Anal. calcd. for $C_8H_{10}N_4O_2 \cdot \frac{1}{2} H_2SO_4$: C, 39.51; H, 4.53; N, 23.05. Found: C, 39.61; H, 4.52; N, 23.18. PMR ($CH_3OH-d_4$+2 drops $CF_3COOH$) γ7.85 (d, 2H, J=8.5 Hz), 7.16 (d, 2H, J=8.5 Hz), 3.20 (t, J=6 Hz, 2H), 2.68 (t, 2H, J=6 Hz).

Part B

4-Aminobenzylguanidine Sulfate

4-Nitrobenzylguanidine sulfate (0.243 g, 1.0 mmol) was dissolved in water (50 ml) by gentle warming and then cooled to ambient temperature. Activated Raney-Nickel catalyst (Wet form, Aldrich Chemical Co.) (500 mg) was added and the mixture was hydrogenated at 50 p.s.i. for 90 min. The catalyst was filtered and washed with water. To the clear, colorless filtrate was added 2N $H_2SO_4$ to pH 1.5. The solution was concentrated to approximately 25 ml; 95% ethanol (150 ml) was added and the solution stored at 4° C. overnight. The colorless needles were filtered and recrystallized from 1N $H_2SO_4$ (8 ml) to give stout prisms (0.205 g, 78%), m.p. 248°–250° C. (dec); IR (cm$^{-1}$) Nujol 3395 (NH), 3260 (NH), 1675 and 1655 (C=N), 1060 (S=O) 835 (1,4 disubstituted benzene); PMR (DMSO-$d_6$) 7.52 (t, 1H, J=5 Hz, $CH_2NH$—), 6.90 (m, 7H) 6.40 (d, 2H, J=8.5 Hz) and 3.98 ($\overline{d, 2H}$, J=5 Hz, $CH_2NH$). Anal. calcd. for $C_8H_{12}N_4 \cdot H_2SO_4$: C, 36.64; H, 5.34; N, 21.37. Found: C, 36.70; H, 5.30; N, 21.39.

Part C.

$^{131}$I-4-Amino-3-Iodobenzylguanidine

Method 1: Chloramine-T Technique

To a 5 ml multi-dose vial containing 0.1–1.0 mg of 4-aminobenzylguanidine sulfate was added 1.0 ml of 0.02M $KH_2PO_4$ buffer (pH 4.8). The mixture was gently warmed (ca. 40° C.) and shaken to obtain a clear solution which was cooled to room temperature. Approximately 10 ml of 0.1N NaOH solution containing 10.0 mCi [$^{131}$I] sodium iodide (New England Nuclear, Boston, MA, carrier-free) was added and the vial was closed with a teflon-lined cap. Chloramine-T (N-chloro-p-toluenesulfonamide, Na salt) (Aldrich Chemical Co.) solution (7.5 μg in 30 μl of 0.02M $KH_2PO_4$ solution was added via syringe with vigorous stirring and the reaction mixture was stirred at ambient temperature for 5 min., and then manually shaken for a few seconds. After stirring for another 5 min., 40 μl of aqueous $NaHSO_3$ solution (1.4 mg/ml) was added, the solution was stirred for 2 min. and then checked by TLC [silica gel:EtOH/EtOAc/conc. $NH_4OH$ (20/20/1)]. The reaction had proceeded to the extent of 95–98%.

The solution was passed through an anion exchange column (Cellex-D, OH⁻ form) under partial vacuum in a closed system to remove the free I-131-iodide. Further elution with 0.005M sodium acetate buffer (3×1 ml) provided the radioactive product which was >99% pure as shown by tlc analysis on silica gel using 1-butanol/acetic acid/water (5/2/1), Rf=0.50, and EtOH/conc. NH$_4$OH (3/1), Rf=0.15. Identity of the radioactive peak was confirmed by Rf coincidence with genuine unlabeled material. The radiochemical yield was 9.5 mCi (95%) and the effective specific activity was 9.5–95.0 mCi/mg.

The I-131-labeled compound showed less than 4% radio-decomposition for up to 14 days when dissolved in pH 4.8 sodium acetate buffer (0.005M) containing 1% (v/v) benzyl alcohol at 4° C. in the dark.

Method 2: Iodo-Gen Technique

First, 4-aminobenzylguanidine sulfate was made as in Example I, Parts A and B. Then, to a 5 ml multi-dose vial was added 100 μl of Iodo-Gen (1,3,4,6-tetrachloro-3γ,6γ-diphenylglycouril) (Pierce Chemical Co., Rockford, Ill.) solution (1.0 mg/ml CH$_2$Cl$_2$). The CH$_2$Cl$_2$ was evaporated under a stream of argon while stirring the solution vigorously with a magnetically driven spin vane. A solution of 4-aminobenzylguanidine sulfate (0.5 mg/0.5 ml) in 0.02M KH$_2$PO$_4$, pH 4.8, was added to the vial. The vial was closed with a teflon-lined cap. Approximately 10 μl of 0.1N NaOH solution containing 10 mCi $^{131}$I-sodium iodide (New England Nuclear, Boston, MA) was added with a Hamilton syringe. The reaction mixture was stirred gently at room temperature for 30 minutes. A purity check by radio-TLC [silica gel: EtOH/EtOAc/conc. NH$_4$OH (20/20/1)] showed that the reaction was greater than 90% complete. The reaction solution was drawn into a 2½ cc sterile syringe. The needle of the syringe was removed and a Swinnex-13 Filter Unit (Millipore Corp., Bedford, MA) containing an Acropor Ion Exchange Filter SB-6407 (Gelman Sciences, Inc., Ann Arbor, MI) was attached. The reaction solution was slowly forced through the filter and into a sterile 10 cc multi-dose vial containing 2.0 ml of 0.005M sodium acetate buffer. Radio-TLC on silica gel using 1-butanol/acetic acid/water (5/2/1), Rf=0.50, and EtOH/conc. NH$_4$OH (3/1), RF=0.15, revealed a radiochemical purity greater than 99%. The radiochemical yield was 8.5 mCi (85% to yield) and the specific activity was 17.0 mCi/mg.

EXAMPLE II $^{123}$I-4-amino-3-iodobenzylguanidine was synthesized in accordance with the following procedure.

First, 4-aminobenzylguanidine sulfate was made as in Example I, Parts A and B. Then, to a 5 ml multi-dose vial containing 0.1–1.0 mg of 4-aminobenzylguanidine sulfate was added 1.0 ml of 0.02M KH$_2$PO$_4$ solution (pH 4.8). The mixture was gently warmed (ca. 40° C.) and shaken to obtain a clear solution which was then cooled to room temperature. Approximately 15 mCi of NaI-123 in 0.10–1.0 ml of 0.1N NaOH (from Crocker Nuclear Laboratories of Davis, Calif.) was added and the vial was closed with a teflon-lined cap.

The reaction was then carried out as in Part C, Method 1, of Example I. Radiochemical yields are as high as obtained for the I-131 method of Example I and the purity determination was the same as reported in Example I.

EXAMPLE III $^{123}$-I-4-amino-3-iodobenzylguanidine was also synthesized in accordance with the following additional procedure.

First, 4-aminobenzylguanidine sulfate was made as in Example I, Parts A and B. Then the procedure in Example I, Part C, Method 2, is carried out except that the radioiodine is $^{123}$I-sodium iodide (15 mCi in 0.1–1.0 ml of 0.1N NaOH from Crocker Nuclear Laboratories of Davis, Calif.) buffered with 0.20M KH$_2$PO$_4$ instead of $^{131}$I-sodium iodide buffered with 0.02M KH$_2$PO$_4$. Radiochemical yield is nearly as high as obtained for the I-131 reaction method of Example I and the radiochemical purity determination was the same as reported in Example I.

EXAMPLE IV $^{125}$I-4-amino-3-iodobenzylguanidine was synthesized in accordance with the following procedure.

First, 4-aminobenzylguanidine sulfate was made as in Example I, Parts A and B. Then, to a 5 ml multi-dose vial containing 0.1–1.0 mg of 4-aminobenzylguanidine sulfate was added 1.0 ml of 0.02M KH$_2$PO$_4$ solution (pH 4.8). The mixture was gently warmed (ca. 40° C.) and shaken to obtain a clear solution which was then cooled to room temperature. Approximately 10 mCi of Na-I-125 in a 5 ml of 0.1N NaOH (from New England Nuclear, Boston, MA) was added and the vial was closed with a teflon-lined cap. The reaction was then carried out as in Part C, Method 1, of Example I. Radiochemical yields are as high as obtained for the I-131 method of Example I and the purity determination was the same as reported in Example I.

EXAMPLE V

In addition to radio-TLC, the radiochemical purity of the foregoing preparations of radioiodinted 4-amino-3-iodobenzylguanidine was determined by radio-HPLC. The radiochemical purity of radioiodinated 4-amino-3-iodobenzylguanidine was routinely found to be >96% on a μBondapak C18 column (THF/0.2M NH$_4$H$_2$PO$_4$, 20/80, 1.5 ml/min). With this HPLC system, the retention times (t$_r$) of the following compounds, which are the most likely chemical impurities, are: iodide (4.5 min), 4-amino-3-iodobenzylamine (6.6 min), 4-amino-3-chlorabenzylguanidine (6.7 min), 3,5-diiodo-4-aminobenzylguanidine (21.1 min). With this HPLC system, the t$_r$ values for 4-aminobenzylguanidine and 4-amino-3-iodobenzylguanidine are 3.8 min and 8.1 min, respectively.

EXAMPLE VI

The chemical identity of radioiodinated 4-amino-3-iodobenzylguanidine was confirmed by synthesis of $^{127}$I-4-amino-3-iodobenzylguanidine by the method described below. This compound had a t$_r$ identical to that of radioiodinated 4-amino-3-iodobenzylguanidine on radio-HPLC the conditions for which are described in Example V.

4-Amino-3-iodobenzylamine

To a solution of (2.44 g, 10 mmol) 4-amino-3-iodobenzonitrile (Helv. Chim. Acta. 54: 1486–1488, 1971, Toth: "Die jodierung von desaktivierten aromatischen aminen in wasseriger phase.") in dry THF (5 ml) was added 30 ml of borane-tetrahydrofuran complex solution (30 mmole) with stirring. The solution was heated at reflux temperature for 1 hr. under argon. Upon cooling, ethanol (2 ml) was added to quench excess borane. After the vigorous reaction subsided, water (30 ml) and ether (40 ml) were added and the mixture was separated. The aqueous layer was again extracted with ether (2×40 ml) and the combined ether extracts were dried. HCl gas was bubbled through the ether solution for 10 min. and the granular white precipitate which resulted was collected and recrystallized from methanol (3.0 g, 94%): mp 185°–195° C. (dec); IR (cm$^{-1}$) Nujol 3500, 1545, 1595 (amine salt); PMR (DMSO-d$_6$) γ8.5 (br, S, 2H), 7.8 (m, 3H), 7.2 (br, S, 2H), 3.7 (S, 2H). Anal. Calcd. for C$_7$H$_9$NI.2HCl: C, 26.17; H, 3.43; N, 8.72. Found: C, 26.21; H, 3.42; N, 8.75.

3-Iodo-4-aminobenzylguanidine

An ethanol (5 ml) solution of 3-iodo-4-aminobenzylamine (0.220 g, 0.887 mmol) and 3,5-dimethylpyrazole-1-carboxamidine nitrate (0.179 g, 0.087 mmol) was heated at reflux temperature for 3 hr. under argon. The solvent was evaporated in vacuo and the residue washed with ether and dichloromethane to remove 3,5-dimethylpyrazole and unreacted amine. The crude product was recrystallized from methanol/ether to give fine, pale-yellow needles (0.163 g, 72.5%), mp 135°–137° C.; PMR (DMSO-d$_6$) γ6.62–7.66 (m, 9H), 4.1 (s, 2H); IR (Nujol) 1660, 1620 cm$^{-1}$ (C≡N); Anal. Calcd. for C$_{18}$H$_{11}$IN$_4$.HNO$_3$.0.5H$_2$O): C, 27.20; H, 3.42, N, 19.08. Found C, 26.70; H, 3.33; N, 19.08.

EXAMPLE VII

Biological tissue distribution studies were performed in rats, dogs, and monkeys injected intravenously with 25 μCi, 100 μCi and 100 μCi, respectively, of I-125 4-amino-3-iodobenzylguanidine in an average volume of 0.2 ml, 2 ml, and 1 ml, respectively. Representative samples of tissues were counted in an autogamma counter with corrections made for radioactive decay, background, and counter efficiency. To normalize for differences in animal weights, tissue concentrations are expressed as percent kilogram dose per gram. The results are set forth below.

| A. Rats (5) at 90 min. (Female Sprague-Dawley): | |
|---|---|
| Tissue | % Kg Dose/g (Mean + S.E.M.) |
| Left Atrium | 0.55 ± .06 |
| Right Atrium | 0.66 ± .05 |
| Left Ventricle | 0.46 ± .05 |
| Right Ventricle | 0.70 ± .02 |
| Blood | 0.08 ± .01 |
| Liver | 0.09 ± .01 |
| Spleen | 0.35 ± .01 |

| B. Female Mongrel Dogs (3): | | | |
|---|---|---|---|
| | To Kg Dose/g (Mean + S.E.M.) | | |
| Tissue | 30 min | 2 hours | 72 hours |
| Adrenal Medulla | 8.80 ± 2.80 | 10.4 ± .8 | 18.3 ± 1.8 |
| Adrenal Cortex | 0.62 ± .16 | 0.51 ± .15 | 0.13 ± .06 |
| Heart (Left Ventricle) | 0.49 ± .05 | 0.52 ± .02 | 0.06 ± .01 |
| Blood | 0.03 ± .00 | 0.03 ± .00 | 0.02 ± .00 |
| Liver | 0.36 ± .02 | 0.20 ± .02 | 0.05 ± .00 |
| Lung | 0.88 ± .61 | 1.26 ± .20 | 0.09 ± .01 |
| Muscle | 0.05 ± .02 | 0.04 ± .01 | 0.01 ± .00 |
| Thyroid | 1.02 ± .06 | 0.85 ± .11 | 14.6 ± 2.4 |

| C. Monkeys (2) at 3 hours: | |
|---|---|
| Tissue | % Kg Dose/g (Mean + S.E.M.) |
| Adrenal Medullae | 1.98 ± .14 |
| Adrenal Cortex | 0.60 ± .04 |
| Heart (Left Ventricle) | 0.85 ± .11 |
| Blood | 0.03 ± .01 |
| Liver | 0.17 ± .04 |
| Lung | 0.99 ± .53 |
| Muscle | 0.03 ± .55 |
| Thyroid | 1.07 ± .55 |

It will be readily apparent that one skilled in the art having benefit of the foregoing disclosure of the present invention may make modifications or variations of the invention without departing from spirit thereof. Therefore, it is intended that the scope of the present invention be limited by the spirit and contents of the appended claims.

What is claimed is:

1. The compound I-4-amino-3-iodobenzylguanidine.
2. A compound of claim 1 wherein I is a isotope selected from I$^{123}$, I$^{131}$ and I$^{125}$.
3. The compound of claim 1 wherein I is the 123 isotope.
4. The compound of claim 1 wherein I is the 131 isotope.
5. A radiopharmaceutical composition comprising radioiodinated I-4-amino-3-iodobenzylguanidine and a carrier.
6. The composition of claim 5 wherein said carrier is a physiological buffered sodium acetate solution.
7. The composition of claim 5 comprising $^{123}$I-4-amino-3-iodobenzylguanidine.
8. The composition of claim 5 comprising $^{131}$I-4-amino-3-iodobenzylguanidine.
9. The composition of claim 7 wherein said $^{123}$I-4-amino-3-iodobenzylguanidine is present in an effective amount of from about 2.0 to about 10.0.
10. The composition of claim 8 wherein said $^{131}$I-amino-3-iodobenzylguanidine is present in an effective amount of from about 0.2 to about 2.0 mCi.
11. The composition of claim 8 wherein said $^{131}$I-4-amino-3-iodobenzylguanidine is present in an effective amount of from about 100 to about 300 mCi.
12. A method of radio-imaging a human organ comprising the steps of:
    (a) systemically applying a pharmaceutical composition comprising radioiodinated 4-amino-3-iodobenzylguanidine to a human;
    (b) detecting gamma radiation emitted by said composition and forming an image therefrom.
13. The method of claim 12 wherein said pharmaceutical composition comprises a physiological buffered sodium acetate carrier.
14. The method of claim 12 wherein said composition comprises $^{123}$I-4-amino-3-iodobenzylguanidine.
15. The method of claim 14 wherein said $^{123}$I-4-amino-3-iodobenzylguanidine is present in an effective amount of from about 2.0 to about 10.0 mCi.
16. The method of claim 12 wherein said composition comprises $^{131}$I-4-amino-3-iodobenzylguanidine.
17. The method of claim 16 wherein said $^{131}$I-4-amino-3-iodobenzylguanidine is present in an effective amount of from about 0.2 to about 2.0 mCi.
18. The method of claim 12 wherein said human organ is selected from the group consisting of the heart, adrenal medulla, and tumors of the adrenal medulla.

19. A method of therapeutically treating a tumor, comprising systemically applying a pharmaceutical composition comprising radioiodinated 4-amino-3-iodobenzylguanidine to a human.

20. The method of claim 19 wherein said composition comprises, in addition, a physiological buffered sodium acetate carrier.

21. The method of claim 19 wherein said composition comprises $^{131}$I-4-amino-3-iodobenzylguanidine.

22. The method of claim 21 wherein said $^{131}$I-4-amino-3-iodobenzylguanidine is present in an effective amount of from about 100 to about 300 mCi.

* * * * *